(12) United States Patent
Bourlion et al.

(10) Patent No.: US 10,624,572 B2
(45) Date of Patent: *Apr. 21, 2020

(54) DEVICES THAT MONITOR PENETRATION OF AN INSTRUMENT IN AN ANATOMICAL STRUCTURE

(75) Inventors: Maurice Bourlion, Saint-Chamond (FR); Dominique Petit, Verton (FR); Gérard Vanacker, Saint-Maur (FR)

(73) Assignee: SpineGuard, Saint-Mande (FR)

( * ) Notice: Subject to any disclaimer, the term of this patent is extended or adjusted under 35 U.S.C. 154(b) by 2096 days.

This patent is subject to a terminal disclaimer.

(21) Appl. No.: 10/589,314

(22) PCT Filed: Feb. 11, 2005

(86) PCT No.: PCT/FR2005/000340
§ 371 (c)(1),
(2), (4) Date: Oct. 11, 2007

(87) PCT Pub. No.: WO2005/077283
PCT Pub. Date: Aug. 25, 2005

(65) Prior Publication Data
US 2008/0269645 A1 Oct. 30, 2008

(30) Foreign Application Priority Data

Feb. 11, 2004 (FR) .................................... 04 01362

(51) Int. Cl.
*A61B 5/053* (2006.01)
*A61B 5/00* (2006.01)
(Continued)

(52) U.S. Cl.
CPC .............. *A61B 5/417* (2013.01); *A61B 5/053* (2013.01); *A61B 17/1626* (2013.01);
(Continued)

(58) Field of Classification Search
CPC .. A61B 5/053; A61B 17/1626; A61B 17/1671
(Continued)

(56) References Cited

U.S. PATENT DOCUMENTS 6,391,005 B1 5/2002 Lum et al.
2003/0105410 A1* 6/2003 Pearlman ..................... 600/547
(Continued)

FOREIGN PATENT DOCUMENTS

| EP | 0 607 688 A1 | | 7/1994 | |
|----|----|----|----|----|
| WO | WO 03/068076 | * | 2/2003 | .................. 600/547 |
| WO | WO 03/068076 | | 8/2003 | |

*Primary Examiner* — Devin B Henson
*Assistant Examiner* — H. Q. Nguyen
(74) *Attorney, Agent, or Firm* — DLA Piper LLP (US)

(57) ABSTRACT

A device to monitor penetration of an instrument in an anatomical structure including at least two electrodes, a source of current supplying the at least two electrodes, and means for measuring impedance between the electrodes, wherein the electrodes are located on the penetration instrument, wherein the first electrode has a contact surface coinciding with a distal surface of the penetration instrument and the second electrode has a contact surface coinciding with a lateral surface of the penetration instrument, and wherein the contact surfaces are dimensioned to have a coinciding and constant contact surface as a function of a degree of penetration of the penetration instrument in the anatomical structure.

7 Claims, 4 Drawing Sheets

(51) Int. Cl.
 *A61B 17/16* (2006.01)
 *A61B 90/00* (2016.01)
(52) U.S. Cl.
 CPC ........ *A61B 17/1671* (2013.01); *A61B 5/4504* (2013.01); *A61B 5/7405* (2013.01); *A61B 2090/08021* (2016.02)
(58) Field of Classification Search
 USPC ........ 600/547, 546, 549, 544, 506; 604/507, 604/117, 272; 607/116
 See application file for complete search history.

(56) References Cited

U.S. PATENT DOCUMENTS

| | | | |
|---|---|---|---|
| 2003/0120328 A1* | 6/2003 | Jenkins et al. ............... | 607/116 |
| 2003/0195423 A1* | 10/2003 | Gibbs et al. ................. | 600/438 |
| 2003/0216663 A1* | 11/2003 | Jersey-Willuhn et al. ... | 600/547 |
| 2004/0193152 A1* | 9/2004 | Sutton ............... | A61B 18/1477 606/48 |

\* cited by examiner

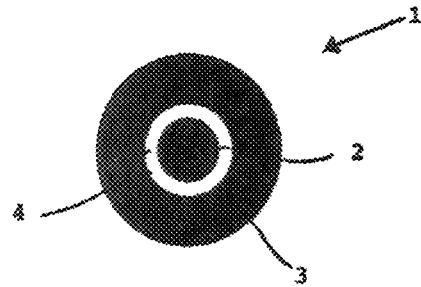
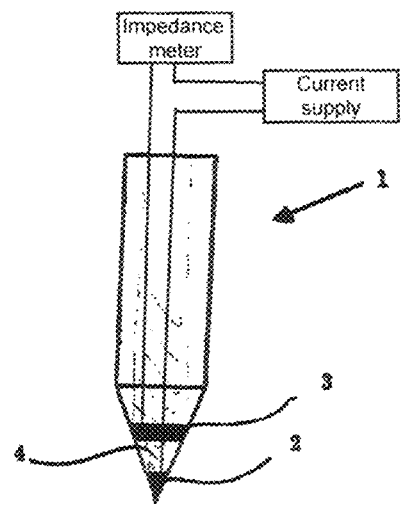
Fig. 1A   Fig. 1B
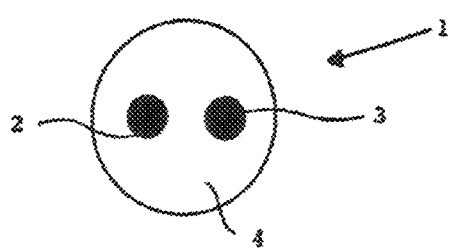
Fig. 2

DEVICES THAT MONITOR PENETRATION OF AN INSTRUMENT IN AN ANATOMICAL STRUCTURE

RELATED APPLICATION

This is a § 371 of International Application No. PCT/FR2005/000340, with an international filing date of Feb. 11, 2005 (WO 2005/077283 A1, published Aug. 25, 2005), which is based on French Patent Application No. 04/01362, filed Feb. 11, 2004.

TECHNICAL FIELD

This disclosure relates to spinal surgery, more particularly, monitoring of penetration instruments during operations of vertebral, cervical, thoracic, lumbar, sacral or iliosacral drilling.

BACKGROUND

Devices used to follow the penetration of an instrument in an anatomical structure, in particular, a bone structure are known.

Ep 0 607 688 describes a procedure and system for the insertion of a pedicular vertebral screw, including applying an electric potential to the surface of the cavity, and observing the muscular reactions provoked by this stimulation.

It is also known to measure the modification in the impedance of the region neighboring the explored bone cavity using a sound presenting an electrode coming into contact with the wall of the bone cavity, and a second electrode placed on the patient. The purpose is to detect the gaps in bone matter, for example, during an operation preparing for the insertion of a pedicular screw in a vertebra.

The information gathered with such an approach is difficult to interpret since the impedance measured between the two electrodes is perturbed by artifacts related to the variation in the penetration of the sound in the cavity. The resistivities of the air, muscle tissue, bone tissue and gaps differ, and the signal measured is the result of several parameters that in part mask the useful information corresponding to the passage of the electrode of the sound near a gap.

In addition, the device is not very practical since it first requires calibration (reference related to soft tissue). Finally, such a device remains not very easy to manipulate due to the presence of external cables.

It could therefore be advantageous to provide a device whose output signal is not disturbed by variations due to the depth of the entry of the penetration instrument.

SUMMARY

This invention relates to a device to monitor penetration of an instrument in an anatomical structure including at least two electrodes, a source of current supplying the at least two electrodes, and means for measuring impedance between the electrodes, wherein the electrodes are located on the penetration instrument, wherein the first electrode has a contact surface coinciding with a distal surface of the penetration instrument and the second electrode has a contact surface coinciding with a lateral surface of the penetration instrument, and wherein the contact surfaces are dimensioned to have a coinciding and constant contact surface as a function of a degree of penetration of the penetration instrument in the anatomical structure.

BRIEF DESCRIPTION OF THE DRAWINGS

Selected, representative aspects of the devices will be better understood upon reading the following description, referring to the appended figures where:

FIGS. 1A and 1B, respectively, are a front sectional view and a longitudinal sectional view of a drilling instrument forming an exploration device;

FIG. 2 is a front sectional view of a drilling instrument;

DETAILED DESCRIPTION

Figure 3:
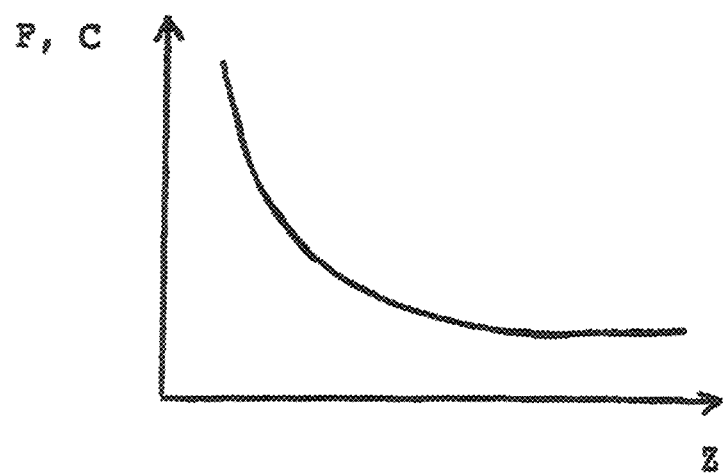
FIG. 3 is a graphic representation of the sound signal given off by the exploration device as a function of the impedance measured.

We disclose devices to monitor penetration of an instrument in an anatomical structure, in particular, a bone structure, comprising a source of current supplying at least two electrodes located on the instrument and a means to measure the impedance between the electrodes. The electrodes are located on the penetration instrument to present a coinciding and constant contact surface as a function of the degree of entry of the penetration instrument in the bone structure.

More precisely, the invariability of the contact surface of the electrodes during entry of the penetration instrument is obtained by the dimensions of the surface with respect to the dimensions of the hole formed in the bone structure by the penetration instrument, since the dimensions of the contact surface should not exceed those of the hole formed by the penetration instrument.

The term "contact surface" refers to the fact that the dimensions of the surface coinciding with the electrodes is smaller than those of the hole formed by the penetration instrument.

Preferably, the device comprises an electrode coinciding with the distal surface of the penetration instrument.

"Distal" surface refers to the surface of the distal end portion of the penetration instrument.

The device may comprise two electrodes coinciding with the distal surface of the penetration instrument, since the electrodes are substantially coaxially placed and separated by insulation.

The device may also comprise two electrodes coinciding with the distal surface of the penetration instrument since the electrodes are symmetrically placed with respect to a longitudinal axis of the penetration instrument.

The device may further comprise a plurality of electrodes coinciding with the distal surface of the penetration instrument.

The device may comprise at least one electrode having a contact surface laterally coinciding with the penetration instrument. Advantageously, the electrode at least has a substantially annular contact surface. Advantageously, the device comprises at least two electrodes having an annular lateral contact surface.

Advantageously, the device may comprise a main electrode coinciding with the distal surface of the penetration instrument as well as a plurality of secondary laterally coinciding electrodes to form longitudinally spaced annular contacts.

The device may also comprise means of signalling producing a signal at the time of detection of a variation in the impedance by the means of measurement.

Advantageously, the signal produced may be a sound signal whose frequency and/or rhythm decreases as a function of the impedance measured. Preferably, the frequency and/or rhythm non linearly reduce as a function of the impedance measured.

Therefore, when the instrument leaves the bone structure, an acute sound signal with a rapid rhythm is produced. When the instrument penetrates and remains in the bone structure, a low-pitched sound signal with a low rhythm is produced.

Advantageously, the device may comprise a central channel for the passage of an additional instrument.

The device monitors penetration of an instrument in the bone structures of a human or animal body, the structures having at least two different zones of electric impedance.

The electrodes, located on the penetration instrument (1), are configured to have a contact surface that remains constant during penetration of the penetration instrument.

The electrodes are each connected to an electric generator delivering an alternative current, which comprises a circuit to measure the impedance between the two electrodes (impedometer).

Therefore, since the impedance of the pedicular tissue is superior that of muscle tissue, the detection of a gap results in a reduction in the impedance.

The device also comprises means for signalling that produce a specific signal at the time of the detection, by impedometer, of a variation in impedance and, therefore, penetration of the instrument in a zone of soft tissue (marrow, nerves), to thereby form a gap in the bone cortex. The means for signalling include emission of a visual signal, such as a light, a sound signal, and/or a tactile signal (vibrator or the like).

A preferred example of the operating principle of the signalling of the detection of a gap is described below and shown in FIG. 3.

In the following section, the penetration instrument includes a drilling instrument (1). However, the configurations presented below are, of course, applicable to other penetration instruments (tapping, curettage, spatulage and the like).

FIGS. 1A and 1B illustrate a first configuration of the drilling instrument (1) composing the exploration device.

In this first configuration, the drilling instrument (1) has, at the distal end portion, two electrodes (2, 3) of circular and concentric section, inner electrode (2) being separated from outer electrode (3) by an insulation ring (4).

Electrode (2) comprises in this example the positive pole of the electronic device, electrode (3) the negative pole. This is only one example of implementation and one skilled in the art may create an electronic device whose positive pole will include electrode (3) and negative pole of electrode (2) without going beyond the scope of this disclosure.

Each electrode (2, 3) is arranged to coincide with the distal surface of the drilling instrument (1).

In order to avoid any perturbation in the signal, the surface of electrode (3) coinciding with the surface of the drilling instrument (1) remains relatively small compared with the dimensions of the hole made in the bone cortex during the drilling operation.

During penetration of the instrument (1) in the bone structure, a signal is given off by the means for signalling when a variation in the impedance measured between the electrodes (2, 3) is detected by the impedometer, indicating formation of a gap.

At that time, the practitioner is informed that the end of the drilling instrument (1) has just left the bone cortex to penetrate in a zone of soft tissue. The practitioner, if so desired, then modifies the path of the drilling instrument (1) to return to the bone cortex.

FIG. 2 illustrates a second configuration of the drilling instrument (1) comprising the exploration device.

In this second configuration, the penetration instrument (1) has two electrodes (2, 3) of sensibly identical circular section its the distal end. The electrodes (2, 3) are advantageously symmetrically arranged with respect to the longitudinal axis of the drilling instrument (1).

Since the position of the electrodes (2, 3) is known, their disposition on the distal end provides indications about the position of the gaps. In fact, the gap detected will be located between the two electrodes (2, 3) for which a signal is emitted.

Since the number and shape of the electrodes is here provided by way of example, it is understood that the penetration instrument (1) may have a greater number of electrodes and their shape may differ. It should be noted that the volumetric detection of gaps will be more exact the higher the number of electrodes distributed at the end of the instrument (1).

FIG. 3 illustrates the graphic representation of the frequency and/or rhythm of a sound signal given off by the means for signalling as a function of the impedance measured between the electrodes.

According to one preferential mode of implementation, the curve corresponding to the frequency and/or rhythm of the signal emitted as a function of the impedance is decreasing and not linear as shown in FIG. 3. Therefore, when the penetration instrument is located in the bone cortex, the impedance measured between the electrodes corresponds to the impedance of the bone, this impedance remains relatively constant. The means for signalling inform the practitioner of the proper position in the cortex by the emission of a signal with a low frequency and slow rhythm. In particular, beyond a certain value of impedance, corresponding to the impedance measured in the bone, the frequency as well as the rhythm of the signal remain relatively constant.

However, when the end of the instrument enters surrounding soft tissue, the practitioner is informed of this by an increase in the frequency and an acceleration in the rhythm of the signal.

Therefore, following this configuration, a small variation of the impedance in the bone is not heard while any variation in the impedance related to the penetration of the instrument in the surrounding soft tissue, as small as it may be, will be strongly heard.

In the same way, it is possible to create penetration instruments having other functionalities.

Figure 7:
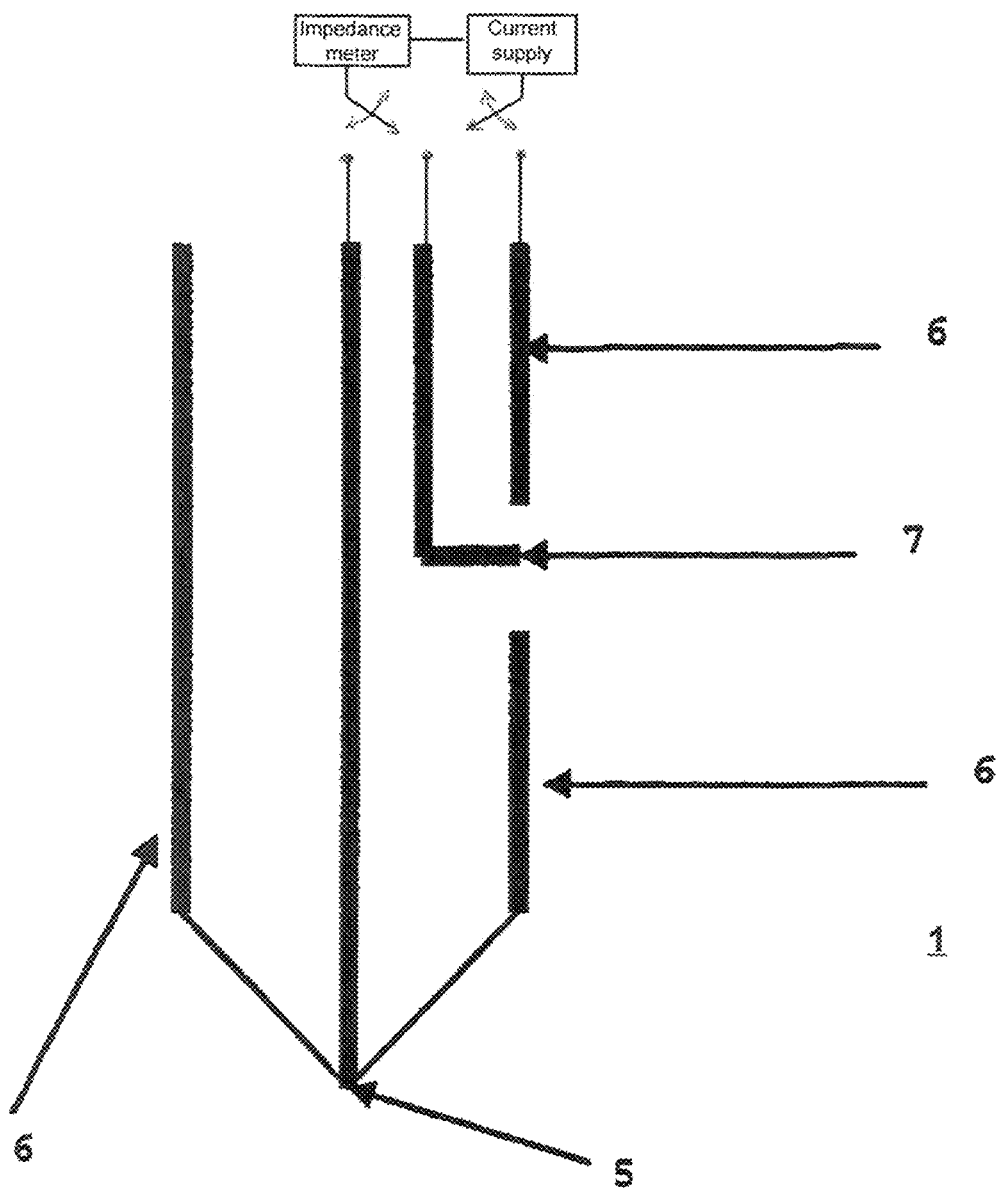
FIG. 7 is a longitudinal sectional view of a penetration instrument of a drilling instrument.

In particular, the drilling instrument (1) may advantageously comprise at least one electrode (7) coinciding with the lateral surface of the drilling instrument (1), as well as two electrodes (5, 6) concentrically arranged at the distal end of the aforementioned drilling instrument (1) (FIG. 7). It will thereby be possible, due to the configuration of the drilling instrument (1), to determine the presence and direction of a gap by means of electrodes (6, 7) as well as signal any perforation of the bone cortex by means of electrodes (5, 6). For this purpose, positioning a lateral electrode comprising a rod going to the distal end should be avoided. In fact, it is believed to be impossible, with such a configuration, to know whether the zone detected by the electrodes is lateral or distal.

Figure 4:
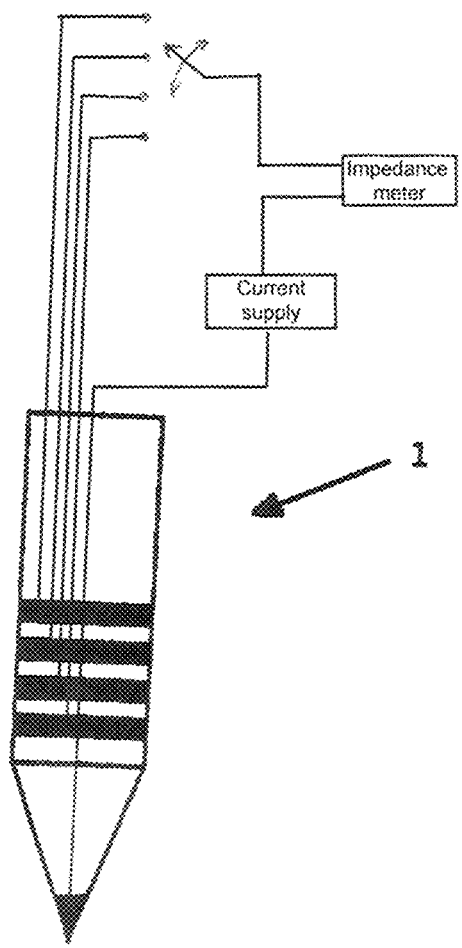
FIG. 4 is a longitudinal sectional view of a drilling instrument.

Advantageously, the electrodes may be arranged on the lateral surface of the drilling instrument to form annular bands of contact coinciding with the surface of the drilling instrument (1) (FIG. 4).

Figure 5:
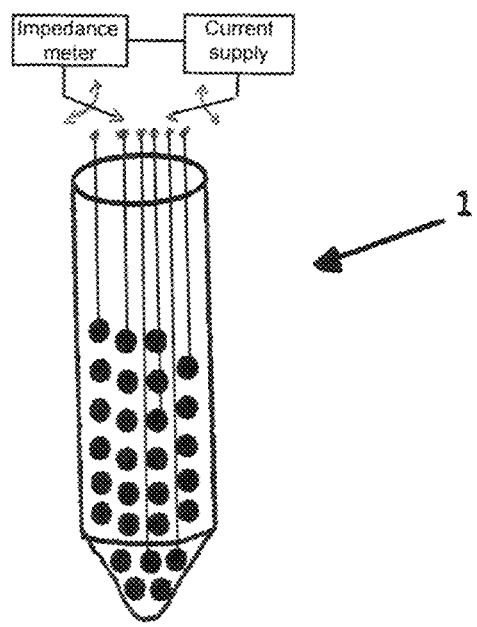
FIG. 5 is a perspective view of a drilling instrument.

The electrodes may be advantageously arranged in the form of points of contact distributed in a homogenous manner on the surface of the drilling instrument (1). Such a distribution of the electrodes enables the volumetric detection of the perforations (FIG. 5). Such a configuration may thereby inform the surgeon of the lowest zone of impedance at all times.

Figure 6:
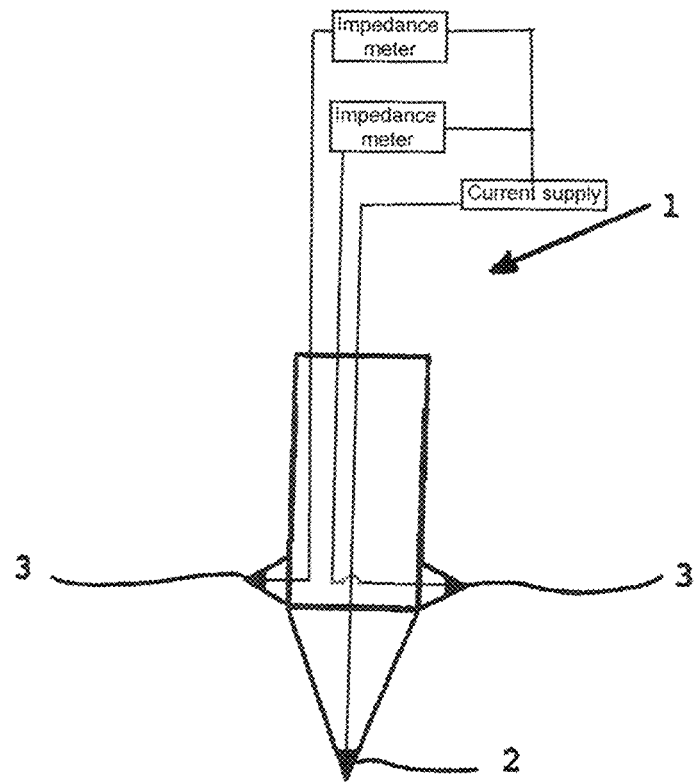
FIG. 6 is a longitudinal sectional view of a penetration instrument comprising a tap.

FIG. 6 also illustrates implementation of a penetration instrument configured for tapping. Advantageously, the instrument (1) comprises a distal end in the form of a point and the lateral wall has cutting stops. One electrode (3) is arranged on at least one cutting stop. At least one other electrode (2) is also arranged at the distal end in point form of the instrument (1). Therefore, during the tapping operation, the surgeon is informed of the formation of a gap in real time not only at the end of the instrument and provoked by the distal end in point form on the instrument (1), but also laterally with respect to the wall of the instrument (1) and provoked by at least one of the cutting stops.

The invention is described above by way of example. It is understood that one skilled in the art is able to create different variants without departing from the framework of the devices as defined in the appended claims.

The invention claimed is:

1. A device that monitors penetration of a penetration instrument in an anatomical structure having at least two zones of different impedances comprising:
    a penetration instrument adapted to form a hole into said anatomical structure having said at least two zones of different impedances, the penetration instrument extending along a longitudinal axis between opposed proximal and distal ends. the penetration instrument having a surface including a cylindrical lateral surface extending from the proximal end, and a frustoconical distal surface at the distal end, the cylindrical lateral surface having a diameter measured transversally with respect to the longitudinal axis;
    at least two electrodes located on the penetration instrument, each of the at least two electrodes having a contact surface coinciding with the surface of the penetration instrument, wherein the at least two electrodes comprise at least one first electrode having the contact surface coinciding with the distal surface of the penetration instrument, and at least two second electrodes having the respective contact surfaces coinciding with the lateral surface of the penetration instrument, wherein the contact surface of each second electrode is annular, the second electrodes forming longitudinally spaced annular contacts;
    a source of current adapted to supply the first and second electrodes;
    an impedance measuring device adapted to measure the impedance between the first and second electrodes during penetration of the penetration instrument into said anatomical structure;
    a signalling device adapted to produce a signal at a time a variation in impedance is detected by the impedance measuring device when the penetration instrument passes from a first of said zones having a first impedance to a second of said zones having a second impedance to inform in real time a practitioner of the position of the penetration instrument;
    wherein the contact surfaces of the first and second electrodes are dimensioned to be constant as a function of a degree of penetration of the penetration instrument in the anatomical structure, said contact surfaces having a dimension measured from the proximal end to the distal end of the penetration instrument along the longitudinal axis that is smaller than the diameter of the cylindrical lateral surface.

2. The device according to claim 1, wherein the at least two electrodes comprise at least two first electrodes that are coaxially arranged and separated from each other by insulation.

3. The device according to claim 1, wherein the at least two electrodes comprise at least two first electrodes that are symmetrical with respect to the longitudinal axis of the penetration instrument.

4. The device according to claim 1, wherein the at least two electrodes further comprise a third electrode partially covering the lateral surface of the penetration instrument.

5. The device according to claim 1, wherein the signal is a sound signal, the signalling device being adapted to decrease a frequency and/or rhythm of the sound signal as a function of impedance measured.

6. The device according to claim 4, wherein the signalling device is adapted to decrease the frequency and/or rhythm in a non-linear manner as a function of the impedance measured.

7. The device according to claim 1, further comprising a central channel adapted for a passage of an additional instrument.

\* \* \* \* \*